US005478955A

United States Patent [19]
DeLuca et al.

[11] Patent Number: 5,478,955
[45] Date of Patent: Dec. 26, 1995

[54] 26,27-DIMETHYLENE-1α,25-DIHYDROXY-VITAMIN D₂ AND 26,27-DIMETHYLENE-24-EPI-1α,25-DIHYDROXYVITAMIN D₂ AND METHODS FOR PREPARING SAME

[75] Inventors: Hector F. DeLuca, Deerfield; Naoshi Nakagawa, Madison, both of Wis.

[73] Assignee: Wisconsin Alumni Research Foundation, Madison, Wis.

[21] Appl. No.: 337,110

[22] Filed: Nov. 10, 1994

Related U.S. Application Data

[62] Division of Ser. No. 70,500, Jun. 2, 1993, Pat. No. 5,397,775, which is a continuation of Ser. No. 813,852, Dec. 26, 1991, abandoned.

[51] Int. Cl.⁶ ........................................ C07J 9/00
[52] U.S. Cl. .................. 552/505; 552/553; 552/548; 556/443; 556/444; 556/446; 556/449; 556/482
[58] Field of Search ..................... 552/553, 548, 552/505; 556/443, 444, 446, 449, 482

[56] References Cited

U.S. PATENT DOCUMENTS

| | | | |
|---|---|---|---|
| 4,588,716 | 5/1986 | DeLuca et al. | 552/653 |
| 4,769,181 | 9/1988 | DeLuca et al. | 552/653 |
| 4,851,401 | 7/1989 | DeLuca et al. | 552/653 |
| 4,973,584 | 11/1990 | DeLuca et al. | 552/653 |

FOREIGN PATENT DOCUMENTS

| | | |
|---|---|---|
| WO91/12239 | 8/1991 | European Pat. Off. . |
| WO89/10351 | 11/1989 | WIPO . |

*Primary Examiner*—Kimberly J. Kestler
*Attorney, Agent, or Firm*—Andrus, Sceales, Starke & Sawall

[57] ABSTRACT

The invention is drawn to cholesterol derivatives in which a cyclopentane ring has been introduced onto the 25-carbon of the side chain and to 24-epimers of these compounds. The compounds are useful intermediates in the production of 26,27-dimethylene-1α,25-dihydroxyvitamin D₂ and 26,27-dimethylene-24-epi-1α,25-dihydroxyvitamin D₂. These vitamin D derivatives are useful for the treatment of diseases such as osteoporosis.

2 Claims, 2 Drawing Sheets

COMPETITIVE BINDING

26,27-DIMETHYLENE-1α, 25-DIHYDROXYVITAMIN D₂ AND 26, 27-DIMETHYLENE-24-EPI-1α, 25-DIHYDROXYVITAMIN D₂ AND METHODS FOR PREPARING SAME

This application is a divisional of application Ser. No. 08/070,500, filed Jun. 2, 1993, now U.S. Pat. No. 5,397,775, which in turn is a continuation of Ser. No. 07/813,852, filed Dec. 26, 1991, now abandoned.

BACKGROUND OF THE INVENTION

With the discovery of 1α,25-dihydroxyvitamin $D_3$ as the active form of the vitamin has come an intense investigation of analogs of this hormonal form of vitamin D with the intent of finding analogs that have selective activity. By now, several compounds have been discovered which carry out the differentiative role of 1,25-dihydroxyvitamin $D_3$ while having little or no calcium activity. Additionally, other compounds have been found that have minimal activities in the mobilization of calcium from bone while having significant activities in stimulating intestinal calcium transport. Modification of the vitamin D side chain by lengthening it at the 24-carbon has resulted in loss of calcium activity and either an enhancement or undisturbed differentiative activity. Placing the 24-methyl of 1α,25-dihydroxyvitamin $D_2$ in the epi-configuration appears to diminish activity in the mobilization of calcium from bone. On the other hand, increased hydrophobicity on the 26- and 27-carbons seems to increase the total activity of the vitamin D compounds provided the 25-hydroxyl is present.

SUMMARY OF THE INVENTION

The present invention provides novel compounds exhibiting a desired, and highly advantageous, pattern of biological activity. These compounds are characterized by a marked intestinal calcium transport activity, as compared to that of 1α,25-dihydroxyvitamin $D_3$, while exhibiting much lower activity than 1α,25-dihydroxyvitamin $D_3$ in their ability to mobilize calcium from bone. Hence, these compounds are highly specific in their calcemic activity. Their preferential activity on intestinal calcium transport and reduced calcium mobilizing activity in bone allows the in vivo administration of these compounds for the treatment of metabolic bone diseases where bone loss is a major concern. Because of their preferential calcemic activity, these compounds would be preferred therapeutic agents for the treatment of diseases where bone formation is desired, such as osteoporosis, osteomalacia and renal osteodystrophy.

Structurally, the key feature of the compounds having these desirable biological attributes is that they are analogs of 1,25-dihydroxyvitamin $D_2$ in which a cyclopentane ring is introduced onto the 25 carbon of the side chain of 1α,25-dihydroxyvitamin $D_2$ and its 24-epimer. Thus, the compounds of this type are characterized by the following general structure:

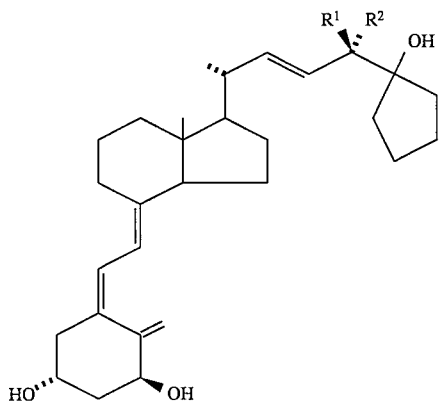

where $R^1$ and $R^2$ may be hydrogen or methyl with the proviso that when $R^1$ is hydrogen $R^2$ cannot be hydrogen and when $R^1$ is methyl $R^2$ cannot be methyl. The present invention, therefore, provides novel compounds showing preferential activity on intestinal calcium transport and reduced calcium mobilizing activity in bone, and are useful for the treatment of metabolic bone disease, such as osteoporosis, where bone loss is a major concern. More specifically, the compounds are 26,27-dimethylene- 1α,25-dihydroxyvitamin $D_2$ and 26,27-dimethylene-24-epi- 1α,25-dihydroxyvitamin $D_2$.

This invention also provides novel intermediate compounds formed during the synthesis of the end products. Structurally, the intermediate compounds are characterized by the following general structure:

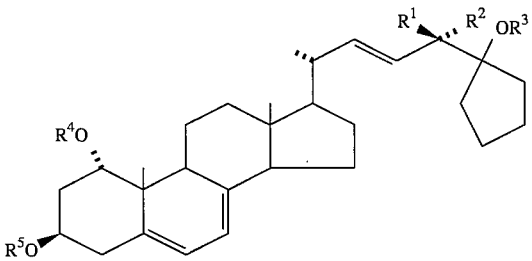

where $R^1$ and $R^2$ may be hydrogen or methyl with the proviso that when $R^1$ is hydrogen $R^2$ cannot be hydrogen and when $R^1$ is methyl $R^2$ cannot be methyl, and $R^3$, $R^4$ and $R^5$ may be hydrogen or a hydroxy-protecting group.

DETAILED DESCRIPTION OF THE INVENTION

Figure 1:
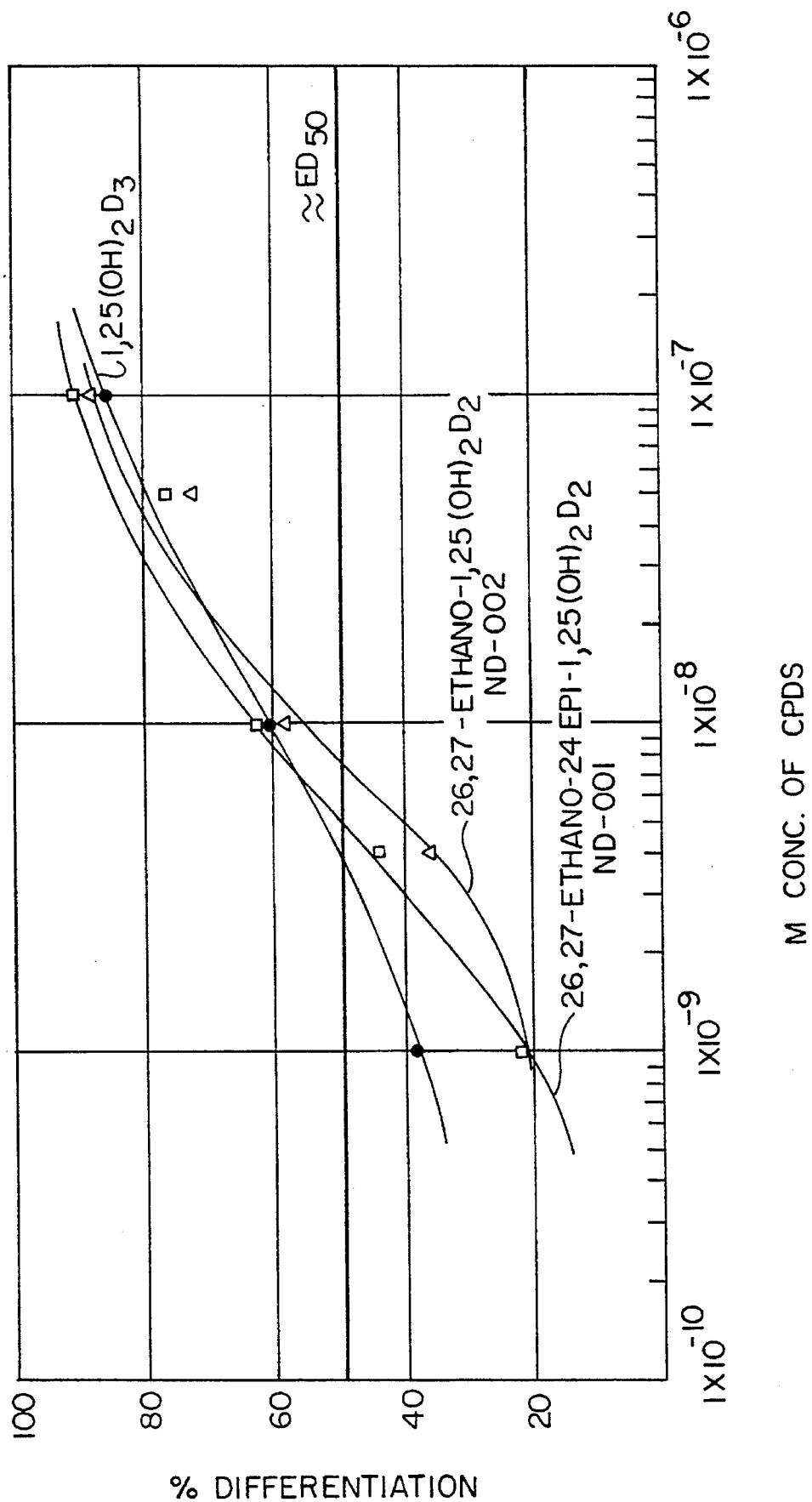
FIG. 1 is a graph illustrating the percent HL-60 cell differentiation as a function of the concentration of 26,27-dimethylene-1α,25-dihydroxyvitamin $D_2$, its 24-epimer and 1α,25-dihydroxyvitamin $D_3$.

As used in the description and in the claims, the term hydroxy-protecting group signifies any group commonly used for the temporary protection of hydroxy functions, such as for example, alkoxycarbonyl, acyl, alkylsilyl, and alkoxyalkyl groups, and a protected hydroxy group is a hydroxy function derivatized by such a protecting group. Alkoxycarbonyl protecting groups are groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term 'acyl' signifies an alkanoyl group of 1 to 6 carbons, in all of its isomeric forms, or a carboxyalkanoyl group of 1 to 6 carbons, such as an oxalyl, maionyl, succinyl, glutaryl group, or a aromatic acyl group such as benzoyl, or a halo, nitro or alkyl substituted benzoyl group. The word 'alkyl' as used in the description or the claims, denotes a straight-chain or branched alkyl radical of 1 to 10 carbons, in all its isomeric forms. Alkoxyalkyl protecting groups are groupings such a methoxymethyl, ethoxymethyl, methoxyethoxymethyl, or tetrahydrofuranyl and tetrahydrofuranyl. Preferred alkylsilyl-protecting groups are trimethylsilyl, triethylsilyl, t-butyldimethylsilyl, and analogous alkylated silyl radicals.

The present invention is more specifically described by the following examples, which are meant to be illustrative only of the process of synthesis and of the novel compounds, both end products and intermediates, obtainable thereby. In these examples, specific compounds identified by Arabic numerals (e.g. compounds 1, 2, 3, . . . etc.) refer to the structures so numbered in the process schematics. Additionally examples are provided which are illustrative of the distinctive biological characteristics of the new compounds, such characteristics serving as a basis for the application of these compounds in the treatment of metabolic bone disease.

Preparation of Compounds

General Procedures

Ultraviolet (UV) absorption spectra were recorded with a Perkin-Elmer Lambda 3b UV-VIS spectrophotometer. Nuclear magnetic resonance (NMR) spectra were recorded at 500 or 400 MHz with Bruker AM-500 multinuclear or AM- 400 wide bore multinuclear spectrometers in the solvents noted. Chemical shifts ($\delta$) are reported downfield from internal $Me_4Si$ ($\delta 0.00$) or $CHCl_3$ ($\delta 7.24$). Low- and high-resolution mass spectra were recorded at 70 eV (unless otherwise stated) on a Kratos MS-50 TC instrument equipped with a Kratos DS-55 Data System. High resolution data were obtained by peak matching. Samples were introduced into the ion source maintained at 120°–250° C. via a direct-insertion probe. Silica gel 60 (Merck, 230–400 mesh) was used for column chromatography. High performance liquid chromatography (HPLC) was performed using a Waters Associates Liquid chromatograph equipped with a model 6000 A solvent delivery system, a Model U6K Universal injector and a model 450 variable wavelength detector. Zorbax Sil Dupont column (4×6 mm×25 cm) was used. Solvent system: 15% 2-propanol in n-hexane. Tetrahydrofuran (THF) was distilled from sodium benzophenone ketyl. Other solvents were purified by standard methods. Reactions involving vitamin D compounds were carried out under a nitrogen atmosphere with magnetic stirring.

Example 1

Synthesis of 26,27-Dimethylene-1α,25-Dihydroxyvitamin $D_2$ (compound 11a) and its 24-epimer (compound 11b) (Process Schemes I and II)

In the synthesis described herein and in Schemes I and II, the following abbreviations are employed:
DHP: 2,3-dihydropyran
PPTS: pyridinium p-toluenesulfonate
THP: 2-tetrahydropyranyl
THF: tetrahydrofuran
Ts: p-toluenesulfonyl
DMAP: 4-dimethylaminopyridine
DMF: N,N-dimethylformamide
Ph: phenyl
mCPBA: m-chloroperbenzoic acid
TES: triethylsilyl
TBAF: tetrabutylammonium fluoride The synthesis of compounds 11a and 11b may be summarized as follows:

The synthesis of side chain sulfones 7a,b started from (R)- or (S)- methyl 3-hydroxy-2-methylpropanate. The hydroxy group was protected to provide 2-tetrahydropyranyl (THP) ester 1. The ester 1 was converted into cyclopentanol 2 by an action of 1,4-dibromomagnesiobutane. The THP protecting group was removed to give diol 3. The primary hydroxy group of the diol was converted to the corresponding p-toluenesulfonate 4. The p-toluenesulfonate 4 was converted into phenylsulfide 5 on treatment with Lhiophenol. The sulfide was oxidized with peracid to sulfone 6. The tertiary hydroxy group was protected as triethylsilyl (TES) ether to give protected sulfone 7.

The sulfone 7 was condensed with aldehyde 9, after deprotonation with lithium diethylamide. The resulting hydroxy sulfone was acetylated, and then submitted to reductive elimination by sodium-amalgam to give (E)-olefin 8. The protective groups of 25- and 3β-hydroxy groups were removed to give provitamin 10. Photo- and thermoisomerization of provitamin 10, followed by deprotection of the 1α-hydroxy group yielded Vitamin D derivative 11.

It should be noted that in the present description and in scheme II, compound 9 is a known compound. Compound 9 may be prepared in accordance with PCT Patent Application No. WO88/07545.

(R)-Methyl 3-(2-tetrahydropyranyl)oxy-2-methylpropanoate 1a.

To a mixture of (R)-(−)-methyl 3-hydroxy-2-methylpropanoate (Aldrich; 4.94 g, 41.8 mmol) and 2,3-dihydropyran (4.22 g, 50.2 mmol) in dichloromethane (100 mL) was added pyridinium p-toluenesulfonate (525 mg, 2.08 mmol) in one portion, and the mixture was stirred at ambient temperature for 2.25 hr. To the mixture 2,3-dihydropyran (1.05 g, 12.5 mmol) was added and the mixture was stirred at ambient temperature for 30 min. The mixture was poured into brine, and the organic layer was separated. The aqueous layer was extracted with diethyl ether, and the combined organic solutions were washed with brine, and dried over sodium sulfate. Filtration and concentration gave 14.83 g of an oily material, which was purified by column chromatography (silica gel 75 g, ethyl acetate in n-hexane, 5–10%) to give 8.20 g (97.0%) of 1a, as a colorless oil.

$^1$H-NMR δ ($CDCl_3$, 500 MHz); 1.12, 1.13 (3H, two d, J=7.0 Hz), 1.38–1.85 (6H), 2.21 (1H, m), 3.32–3.91 (4H), 3.63 (3H, br s), 4.54 (1H, dd, J=12.0 and 2.9 Hz)

(S)-Methyl 3-(2-tetrahydropyranyl)oxy-2-methylpropanoate 1b.

In the same manner as for 1a, (S)-(−)-methyl 3-hydroxy-2-methylpropanoate (Aldrich; 4.96 g, 42.0 mmol) was converted into 8.38 g (98.7%) of 1b, as a colorless oil, which showed virtually the same $^1$H-NMR spectrum as 1a.

(R)-1-[1-(2-Tetrahydropyranyl) oxy-2-propyl]-1-cyclopentanol 2a.

To an ice-cooled and stirred solution of 1,4-bisbromomagnesiobutane (prepared from 1.24 g of magnesium turnings and 5.03 g of 1,4-dibromobutane in 55 mL of tetrahydrofuran) was added a solution of 1a (4.0 g, 19.8 mmol) in diethyl ether (30 mL) dropwise at 0°–25° C. under nitrogen over 70 min. The mixture was stirred at ambient temperature for 2 hr, and then quenched by the addition of ammonium chloride solution. The organic layer was separated, and the aqueous layer was extracted with diethyl ether. The combined organic layers were washed with brine, and dried over sodium sulfate. Filtration and concentration gave 5.98 g of an oily material, which was purified by column chromatography (silica gel 60 g, ethyl acetate in n-hexane, 2.5–20%) to give 3.58 g (79.3%) of 2a, as a colorless oil.

$^1$H-NMR δ (CDCl$_3$, 500 MHz); 1.00, 1.02 (3H, two d, J=7.3 Hz), 1.38–1.93 (15H), 3.04 (1H, d, J=16.2 Hz), 3.35 (0.5H, dd, J=9.8 and 4.9 Hz), 3.42–3.56 (1.5H), 3.73–3.85 (1.5 H), 3.97 (0.5 H, dd, J=9.6 and 4.7 Hz), 4.55 (1H, d, J=14.9 Hz)

(S) -1-[1-(2-Tetrahydropyranyl) oxy-2-propyl] -1-cyclopentnol 2b

In the same manner as for 2a, 1b (3.0 g. 14.8 mmol) was converted into 3.58 g (quantitative) of 2b, as a colorless oil, which showed virtually the same $^1$H-NMR spectrum as 2a.

(R) -1(1-Hydroxy-2-propyl)-1-cyclopentanol 3a

A mixture of 2a (3.42 g, 15.0 mmol) and pyridinium p-toluenesulfonate (188 mg) in ethanol (100 mL) was heated at 40°–50° C. with stirring for 10 hr. The mixture was diluted with toluene and a small amount of triethylamine was added to the mixture. After evaporation of ethanol, the residue was poured into brine and extracted with ethyl acetate until none of the product remained the in aqueous layer. The combined organic layers were washed with brine, and dried over sodium sulfate. Filtration and concentration gave 2.53 g of an oily material, which was purified by column chromatography (silica gel 20 g, ethyl acetate in n-hexane, 20–50%) to give 1.88 g (86.9%) of 3a, as a colorless oil.

$^1$H-NMR δ (CDCl$_3$, 500 MHz); 0.97 (3H, d, J=7.2 Hz), 1.38–1.86 (9H), 3.44 (1H, br s), 3.60 (1H, dd, J=9.7 and 4.8 Hz), 3.81 (1H, d, J=8.0 Hz), 3.93 (1H, br s)

(S)-1-(1-Hydroxy-2-propyl)-1-cyclopentanol 3b

In the same manner as for 3a, 2b (3.41 g, 14.9 mmol) was converted into 1.98 g (92.1%) of 3b, as a colorless oil, which showed the same $^1$H-NMR spectrum as 3a.

(R)-1-(1-p-Toluenesulfonyloxy-2propyl)-1-cyclopentanol 4.

A mixture of 3a (1.79 g, 12.4 mmol), pyridine (5 mL), and p-toluenesulfonyl chloride (4.26 g, 22.3 mmol) in dichloromethane (40 mL) was stirred below 10° C. for 2 days. The reaction mixture was poured into copper (II) sulfate solution and extracted with diethyl ether. The combined organic layers were washed with copper (II) sulfate solution, water, sodium bicarbonate solution and brine, and dried over sodium sulfate. Filtration and concentration gave 6.27 g of an oily material, which was purified by column chromatography (silica gel 60 g, ethyl acetate in n-hexane, 5–33%) to give 3.74 g (quantitative) of 4a as a colorless oil.

$^1$H-NMR δ (CDCl$_3$, 500 MHz); 0.95 (3H, d, J=6.8 Hz), 1.28–1.92 (9H), 2.42 (3H, s), 3.91 (1H, dd, J=9.6 and 7.8 Hz), 4.18 (1H, dd, J=9.6 and 4.6 Hz), 7.32 (2H, d, J=8.0 Hz), 7.75 (2H, d, J=8.0 Hz)

(S)-1-(1-p-Toluenesulfonyloxy-2-propyl)-1-cyclopentanol 4b.

In the same manner as for 4a, 3b (1.92 g, 13.3 mmol) was converted into 3.46 g (87.2%) of 4b, as a colorless oil, which showed the same $^1$H-NMR spectrum as 4a.

(S)-1-(1-Benzenesulfenyl-2-propyl)-1-cyclopentanol 5a

To a mixture of 4a (3.65 g, 11.9 mmol) and triethylamine (2.5 mL) in N,N-dimethylformamide (18 mL) was added thiophenol (1.8 mL) in one portion. The mixture was stirred at ambient temperature overnight. The mixture was poured into water, and extracted with diethyl ether. The combined organic layers were washed with sodium bicarbonate solution and brine, and dried over sodium sulfate. Filtration and concentration gave 3.26 g of an oily material, which was purified by column chromatography (silica gel 40 g, ethyl acetate in n-hexane, 2.5–20%) to give 2.06 g (73.3%) of 5a, as a pale yellow oil. $^1$H-NMR δ (CDCl$_3$, 500 MHz); 1.24 (3H, d, J=6.3 Hz), 1.53 (1H, br s), 1.56–2.04 (9H), 2.85 (1H, dd, J=12.9 and 10.2 Hz), 3.44 (1H, dd. J=12.9 and 2.8 Hz), 7.28 (1H, t, J=8.0 Hz), 7.39 (2H, t, J=8.0 Hz), 7.46 (2H, d, J=8.0 Hz)

(R)-1-(1-Benzenesulfenyl-2-propyl)-1-cyclopentanol 5b

In the same manner as for 5a, 4b (3.65 g, 11.9 mmol) was converted into 2.23 g (82.8%) of 5b, as a pale yellow oil, which showed the same $^1$H-NMR spectrum as 5a.

(S)-1-(1-Benzenesulfonyl-2-propyl)-1-cyclopentanol 6a

To a stirred and ice-cooled mixture of 5a (2.06 g, 8.71 mmol) in dichloromethane (19 mL) and saturated sodium bicarbonate solution (28 mL) was added m-chloroperbenzoic acid (85%, 4.24 g, 20.9 mmol) portionwise. The mixture was stirred in an ice bath for 50 min. An excess amount of peracid was decomposed with sodium thiosulfate solution in the presence of a small amount of potassium iodide. The organic layer was separated, and the aqueous layer was extracted with ethyl acetate. The combined organic layers were washed with sodium bicarbonate solution and brine, and dried over sodium sulfate. Filtration and concentration gave 3.16 g of an oily material, which was purified by column chromatography (silica gel 32 g, ethyl acetate in n-hexane, 20–33%) to give 2.43 g (quantitative) of 6a, as a colorless oil.

$^1$H-NMR δ (CDCl$_3$, 400 MHz); 1.17 (3H, d, J=6.8 Hz), 1.46–1.86 (8H), 2.18 (1H, m), 3.00 (1H, dd, J=14.5 and 9.0 Hz), 3.41 (1H, br d, J=14.5 Hz), 7.57 (2H, t, J=7.3 Hz), 7.65 (1H, t, J=7.3 Hz), 7.92 (2H, d, J=7.3 Hz)

(R)-1-(1-Benzenesulfonyl-2-propyl)-1-cyclopentanol 6b

In the same manner as for 6a, 5b (2.23 g, 9.43 mmol) was converted into 2.34 g ( 92.5% ) of 6b, as a colorless oil, which showed the same $^1$H-MMR spectrum as 6a.

(S)-1-(1-Benzenesulfonyl-2-propyl)-1-triethylsiloxy-cyclopentane 7a

To a solution of 6a (2.40 g, 8.94 mmol) and imidazole (1.22 g, 17.9mmol) in N,N-dimethylformamide (20 mL) was added chlorotriethylsilane (2.2 mL, 13.1 mmol) in one portion. The mixture was stirred at ambient temperature for 3d. The mixture was poured into ice water, and extracted with diethyl ether. The combined organic layers were washed with water and brine, and dried over sodium sulfate. Filtration and concentration gave 4.24 g of an oily material, which was purified by column chromatography (silica gel 40 g, ethyl acetate in n-hexane, 10%) to give 3.67 g (quantitative) of 7a, as a colorless oil.

$^1$H-NMR δ (CDCl$_3$, 500 MHz); 0.52 (6H, q, J=7.9 Hz), 0.88 (9H, t, J=7.9 Hz), 1.11 (3H, d, J=6.7 Hz), 1.35– 1.74 (8H), 2.06 (1H, m), 2.90 (1H, dd, J=14.4 and 9.7 Hz), 3.42 (1H, d, J=14.4 Hz), 7.56 (2H, t, J=7.5 Hz), 7.64 (1H, t, J=7.5 Hz), 7.91 (2H, d, J=7.5 Hz )

(R)-1-(1-Benzenesulfonyl-2-propyl)-1-triethylsiloxycyclo pentane 7b

In the same manner as for 7a, 6b (2.20 g, 8.19 mmol) was converted into 3.19 g (quantitative) of 7b, as a colorless oil, which showed the same $^1$H-NMR spectrum as 7a.

(22E, 24R)-26,27-Dimethylene-1α,3β-bis (methoxycarbonyloxy)-25-triethylsiloxyergosta-5,7,22-triene 8a.

To a stirred solution of 7a (1.0 g, 2.61 mmol) in tetrahydrofuran (30 mL) was added a solution of lithium diethylamide (prepared from 0.44 mL of diethylamine and 2.5 mL of 1.6N n-butyllithium in 7 mL of tetrahydrofuran; 6.6 mL) dropwise at −50°–60° C. under nitrogen. The mixture was stirred at −50°–60° C. for 1 hr, and then cooled to −78° C. To the mixture was added a solution of (20S)-1α, 3β-bis-(methoxycarbonyloxy)-20-methylpregna-5,7-dien-21 -al 9 (670 mg, 1.45 mmol) in tetrahydrofuran (20 mL) dropwise over a period of 50 min. The mixture was stirred for 50 min, and then quenched by the addition of saturated ammonium chloride solution and ethyl acetate. The organic layer was separated and the aqueous layer was extracted with ethyl acetate. The combined organic layers were washed with brine, and dried over sodium sulfate. Filtration and concentration gave 2.97 g of a residue. The residue was dissolved in dichloromethane (20 mL) and to the solution was added 4-dimethylaminopyridine (2.12 g, 17.4 mmol) and acetic anhydride (1.3 mL, 13.8 mmol), and the mixture was stirred at ambient temperature overnight. The mixture was poured into a mixture of ice and ethyl acetate, and the organic layer was separated. The aqueous layer was extracted with ethyl acetate, and the combined organic layers were washed with brine and dried over sodium sulfate. Filtration and concentration gave 2.37 g of a residue. The residue was dissolved in a mixture of tetrahydrofuran (30 mL) and methanol (30 mL) and the solution was stirred at −40° to −30° C. To the solution was added sodium bicarbonate (2.27 g) and 5% sodium amalgam (pulverized and washed with tetrahydrofuran; 10.72 g). The mixture was stirred at −40° to −30° C. for 2.5 hr. The supernatant was filtered through a pad of Celite and the solids was washed with ethyl acetate. The combined organic solution was poured into a cold mixture of diluted hydrochloric acid and ethyl acetate, and the organic layer was separated. The aqueous layer was extracted with ethyl acetate and the combined organic layers were washed with brine, and dried over sodium sulfate. Filtration and concentration gave 2.75 g of a residue, which was purified by column chromatography (silica gel 50 g, ethyl acetate in n-hexane, 5–50%) to give 648 mg (65.2% from 9) of 8a, as white solids.

$^1$H-NMR δ (CDCl$_3$, 500 MHz); 3.77 (3H, s), 3.78 (3H, s), 4.84 (1H, br s), 4.89 (1H, m), 5.20 (1H, dd, J=15.2 and 8.5 Hz), 5.30 (1H, dd, J=15.2 and 8.6 Hz), 5.36 (1H, m), 5.67 (1H, m)

(22E, 24S)-26,27-Dimethylene-1α,3β-bis(methoxycarbonyloxy)-25-triethylsiloxyergosta-5,7,22-triene 8b In the same manner as for 8a, 7b (1.0 g, 2.61 mmol) was converted into 803 mg (67.4% form 9) of 8b, as white solids.

$^1$H-NMR δ (CDCl$_3$, 500 MHz); 3.77 (3H, s), 3.79 (3H, s), 4.84 (1H, br s), 4.90 (1H, m), 5.21 (1H, dd, J=15.3 and 8.3 Hz), 5.30 (1H, dd, J=15.3 and 8.4 Hz), 5.37 (! H, m), 5.68 (1H, m)

(22E,24R)-26,27-Dimethylene-1α-methoxycarbonyloxyergosta-5,7,22-triene-3β,25-diol 10a To a solution of 8a (597 mg, 0.871mmol) in tetrahydrofuran (12 mL) was added 1M solution of tetrabutylammonium fluoride in tetrahydrofuran (4.4 mL), and the mixture was stirred at ambient temperature overnight. The mixture was poured into cold brine, and extracted with ethyl acetate. The combined organic layers were washed with sodium bicarbonate solution and brine, and dried over sodium sulfate. Filtration and evaporation gave 0.78 g of a residue. To the residue was added methanol (50 mL) and potassium carbonate (0.5 g) and the mixture was stirred in a cold room (at 8° C.) overnight. The mixture was poured into cold brine and extracted with ethyl acetate.

The combined organic layers were washed with brine, and dried over sodium sulfate. Filtration and concentration gave 1.54 g of a residue, which was purified by column chromatography (silica gel 30 g, ethyl acetate in n-hexane, 20–80%) to give 313 mg (70.1%) of 10a, as white solids.

$^1$H-NMR δ (CDCl$_3$, 500 MHz); 0.62 (3H, s), 1.00 (3H, s), 1.02 (3H, d, J=6.7 Hz), 1.03 (3H, d, J=6.2 Hz), 3.78 (3H, s), 3.99 (1H, br), 4.82 (1H, br s), 5.33 (2H, m), 5.36 (1H, m), 5.66 (1H, m)

(22E,24S)-26,27-Dimethylene-1α-methoxycarbonyloxyergosta-5,7,22-triene-3β,25-diol 10b In the same manner as for 10a, 8b (588 mg, 0.858 mmol) was converted into 302 mg (68.7%) of 10b, as white solids.

$^1$H-NMR δ (CDCl$_3$, 500 MHz); 0.63 (3H, s), 1.01 (3H, s), 1.03 (3H, d, J=6.8 Hz), 1.04 (3H, d, J=6.5Hz), 3.78 (3H, s), 4.00 (1H, m), 4.82 (1H, br s), 5.34 (1H, dd, J=15.4 and 8.2 Hz), 5.37 (1H, m), 5.40 (1H, dd, J=15.4 and 7.4 Hz), 5.67 (1H, m)

(5Z,7E,22E,24R)-26,27-Dimethylene-9,10-secoergosta-5,7,10 (19), 22-tetraene-1α,3β,25-triol 11a A stirred and ice-cooled solution of 10a (103 mg, 0.201 mmol) in a mixture of diethyl ether (100 mL) and benzene (20 mL) was irradiated with medium pressure mercury lamp for 30 min under nitrogen. The mixture was concentrated under reduced pressure and the residue was dissolved in benzene (20 mL) and left to stand at ambient temperature for 15d under nitrogen covered with aluminum foil. The mixture was concentrated under reduced pressure, and the residue was treated with 1% lithium hydroxide hydrate solution in methanol (5 mL) at ambient temperature for 1 hr under nitrogen. The mixture was poured into ice water, and extracted with ethyl acetate. The combined organic layers were washed with brine, and dried over sodium sulfate. Filtration and concentration under reduced pressure gave an oily material, which was purified by column chromatography (silica gel 10 g, ethyl acetate in n-hexane. 33–80%) to give 37.6 mg (36.5%) of 10a and 27.4 mg (30.0%, 47.2% based on recovery of 10a) of 11b, as white solids.

UV (ethanol); $\lambda$max 266 nm, $\lambda$min 228 nm MS (EI) m/z 454 (M+), 436 (M+–H2O), 418 (M+–2H$_2$O), 400 (M+–3H$_2$O), 370 (M++1-C$_5$H$_9$O), 352 (M++1-C$_5$H$_9$O-H$_2$O), 334 (M++1-C$_5$H$_9$O-2H$_2$O), 285 (M++1-C$_9$H$_{12}$O$_2$ -H$_2$O), 269 (M+-C$_{11}$H$_{19}$O-H$_2$O), 152 (C$_9$H$_{12}$O$_2$), 85 (base peak, C$_5$H$_9$O) HRMS m/z; Found 454.3434, Calcd. for C$_{30}$H$_{46}$O$_3$ 454.3447

$^1$H-NMR $\delta$ (CDCl$_3$, 500 MHz); 0.55 (3H, s), 1.01 (3H, d, J=6.9 Hz), 1.02 (3H, d, J=6.4 Hz), 4.23 (1H, br s), 4.43 (1H, m), 4.99 (1H, s), 5.36–5.42 (3H), 6.01 (1H, d, J=11.3 Hz), 6.38 (1H, d, J=11.3 Hz) HPLC T$_R$ (min); 12.0

(5Z,7E, 22E,24S)-26,27-Dimethylene-9,10-secoergosta-5, 7,10 (19), 22tetraene-1$\alpha$,3$\beta$,25-triol 11b

In the same manner as for 11a, 11b (100 mg, 0.195 mmol) was converted into 23.5 mg (26.5%, 55.4% based on recovery of 10b) of 11b, as white solids, and 52.2 mg (52.2%) of 10b was recovered.

U V (ethanol); $\lambda$max 266 nm, $\lambda$min 228 nm MS (EI) m/z; 454 (M$^+$), 436 (M+-H$_2$O), 418 (M+-2H$_2$O), 352 (M++1 -C$_5$H$_2$O-H$_2$O), 334 (M++1-C$_5$H$_9$O-2H$_2$O), 285 (M++1-C$_9$H$_{12}$O$_2$-H$_2$O), 269 (M+-C$_{11}$H$_{19}$O-H$_2$O), 152 (C$_9$H$_{12}$O$_2$), 85 (base peak, C$_5$H$_9$O) HRMS m/z; Found 454.3472, Calcd. for C$_{30}$H$_{46}$O$_3$ 454.3447

$^1$H-NMR $\delta$ (CDCl$_3$, 500 MHz); 0.56 (3H, s), 1.03 (6H, d, J=7.0 Hz), 4.23 (1H, br s), 4.43 (1H, m), 5.00 (1H, s), 5.32 (1H, s), 5.35 (1H, dd, J=15.4 and 7.6 Hz), 5.38 (1H, dd, J=15.4 and 6.8 Hz), 6.01 (1H, d, J=11.3 Hz), 6.38 (1H, d, J=11.3 Hz) HPLC T$_R$ (min); 12.1

Biological Activity of 26,27-Dimethylene-1$\alpha$,25-Dihydroxyvitamin D$_2$ (Compound 11b) and its 24-epimer (compound 11a) Example 2—Calcemic Activity Weanling male rats obtained from the Holtzman Company were fed a low calcium (0.02%), 0.3% phosphorus, vitamin D-deficient diet for three weeks. After this time, the animals were severely hypocalcemic. They were then implanted with Alzet minipumps that delivered approximately 13 $\mu$L of solution per day which contained the indicated dose in Table 1 dissolved in 5% ethanol, 95% propylene glycol. After 7 days the rats were killed and the duodena were used for determination of intestinal calcium transport by the everted intestinal sac technique (Martin & DeLuca, 1967) and serum calcium (bone calcium mobilization). The tests were made against 1,25-dihydroxyvitamin D$_3$ and are reported in Table 1.

TABLE 1

INTESTINAL CALCIUM TRANSPORT AND BONE CALCIUM MOBILING ACTIVITIES OF 26,27-DIMETHYENE-1$\alpha$,25-DIHYDROXYVITAMIN D2 AND 26, 27-DIMETHYENE-24-EPI-1$\alpha$,25-DIHYDROXYVITAMIN D$_2$

| Treatment | Doses (pmoles/day) | Intestinal Calcium Transport Serosal/Mucosal | Bone Calcium Mobilization (Serum Calcium) (mg/100 ml) |
|---|---|---|---|
| None | 0 | 3.0 ± 0.2 | 4.2 ± 0.2 |
| 1,25-(OH)$_2$D$_3$ | 130 | 8.5 ± 0.9 | 5.7 ± 0.3 |
| Dimethylen-1,25-(OH)$_2$D$_2$ | 130 | 5.2 ± 0.4 | 4.4 ± 0.1 |
|  | 325 | 6.6 ± 0.6 | 5.8 ± 0.1 |
| Dimethylen-24-epi-1,25-(OH))$_2$D$_2$ | 130 | 6.3 ± 0.3 | 4.4 ± 0.1 |
|  | 325 | 7.8 ± 0.1 | 5.1 ± 0.4 |

The results show that the dimethylene-1,25-dihydroxyvitamin D$_2$ and the dimethylene-24-epi-1,25-dihydroxy-vitamin D$_2$ are both less active than 1,25-dihydroxy-vitamin D$_3$ in both the mobilization of calcium from bone and intestinal calcium transport. However, both of the 26,27-dimethylene-D$_2$ compounds have highly significant intestinal calcium transport activity. The amount of bone calcium mobilizing activity is considerably less than 1,25-dihydroxyvitamin D$_3$, and in the case of the 24-epi-compound, it is considerably less active in this regard. These compounds, therefore, by showing preferential activity on intestinal calcium transport and reduced calcium mobilizing activity in bone suggest that they disease where bone loss is a major issue, such as osteoporosis, osteomalacia and renal osteodystrophy.

Example 3—Measurement of Differentiation in HL-60 Cells

The measurement of differentiation in HL-60 cells (human leukemia cells) was carried out according to the general procedures described by DeLuca et al., U.S. Pat. No. 4,717,721. As shown in Table 2, degree of differentiation is assessed by a standard assay, namely, NBT reduction, and results are expressed as the percent of differentiated cells produced in response to treatment with various concentrations of vitamin D compounds.

TABLE 2

Differentiation Activity in HL-60 Cells in Culture

| Compound | Concentration (molar) | % Cells Showing Differentiation NBT Reduction |
|---|---|---|
| 1,25-(OH)$_2$D$_3$ | 1 × 10$^{-7}$ | 86 ± 3 |
|  | 1 × 10$^{-8}$ | 61 ± 3 |
|  | 1 × 10$^{-9}$ | 38 ± 4 |
| 26,27-Dimethylen-1,25-(OH)$_2$D$_2$ | 1 × 10$^{-7}$ | 89 ± 3 |
|  | 5 × 10$^{-8}$ | 73 ± 4 |
|  | 1 × 10$^{-8}$ | 59 ± 4 |
|  | 5 × 10$^{-9}$ | 36 ± 4 |
|  | 1 × 10$^{-9}$ | 23 ± 2 |
| 26,27-Dimethylen-24-epi-1,25-(OH)$_2$D$_2$ | 1 × 10$^{-7}$ | 90 ± 3 |
|  | 5 × 10$^{-8}$ | 77 ± 2 |
|  | 1 × 10$^{-8}$ | 63 ± 4 |
|  | 5 × 10$^{-9}$ | 44 ± 4 |
|  | 1 × 10$^{-9}$ | 21 ± 2 |

[a]Standard error of the mean of 3-4 determinations.

The results of this assay is shown in Table 2. It is evident that the novel analogs (compounds 11a and 11b) are about equally as active as 1,25-(OH)$_2$D$_3$ itself in causing differentiation of HL-60 cells in culture.

Figure 2:
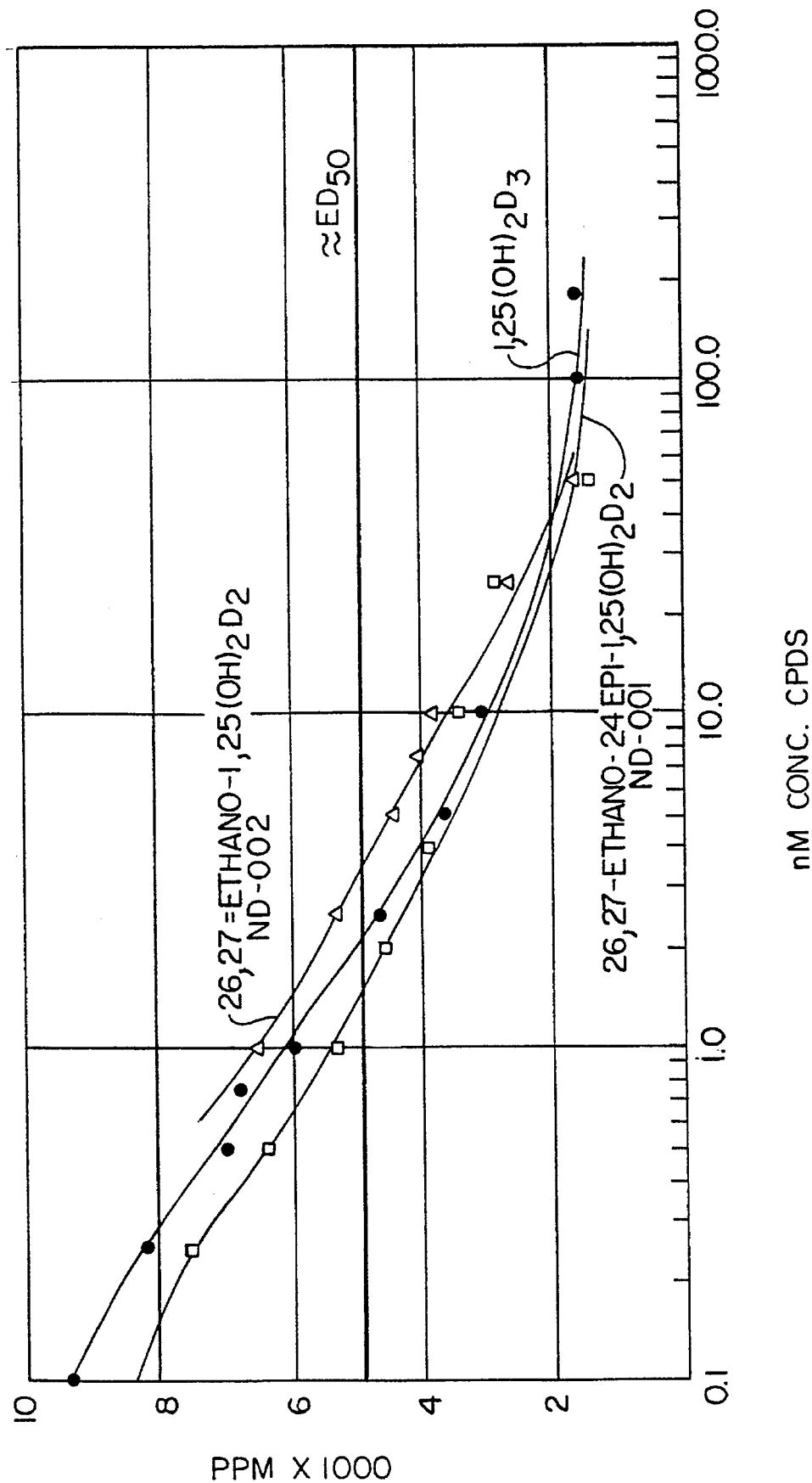
FIG. 2 is a graph illustrating the relative activity of 26,27-dimethylene-16 ,25-dihydroxyvitamin $D_2$, its 24-epimer and 1α,25-dihydroxyvitamin $D_3$ in binding to the 1,25-dihydroxyvitamin D pig intestinal nuclear receptor.

The results shown in FIG. 1 illustrate that these compounds when added to cultures of human HL-60 cells cause their differentiation into monocytes and show activity approximately equal to 1α,25-dihydroxyvitamin $D_3$. FIG. 2 shows both 26,27-dimethylene- 1,25-dihydroxyvitamin $D_2$ and its 24-epimer are at least equal in activity to 1,25-$(OH)_2D_3$ in binding to the 1,25-$(OH)_2D$ pig intestinal nuclear receptor.

Because these compounds are at least as active as 1,25-$(OH)_2D_3$ in differentiation, receptor binding, and approximately equal in intestinal calcium transport activity but are very much less active in mobilizing bone calcium, they would appear to be ideal for treatment of diseases where bone formation is desired.

For treatment purposes, the novel compounds of this invention may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and nontoxic excipients such as stabilizers, anti-oxidants, binders, coloring agents or emulsifying or taste-modifying agents.

The compounds may be administered orally, parenterally or transdermally. The compounds are advantageously administered by injection or by intravenous infusion of suitable sterile solutions, or in the form of liquid or solid doses via the alimentary canal, or in the form of creams, ointments, patches, or similar vehicles suitable for transdermal applications. Doses of from 0.5 μg to 50 μg per day of the compounds are appropriate for treatment purposes, such doses being adjusted according to the disease to be treated, its severity and the response of the subject as is well understood in the art. Since the new compounds exhibit specificity of action, each may be suitably administered alone, in situations where only calcium transport stimulation is desired, or together with graded doses of another active vitamin D compound—e.g. 1α-hydroxyvitamin $D_2$ or $D_3$, or 1α,25-dihydroxyvitamin $D_3$—in situations where some degree of bone mineral mobilization (together with calcium transport stimulation) is found to be advantageous.

SCHEME I

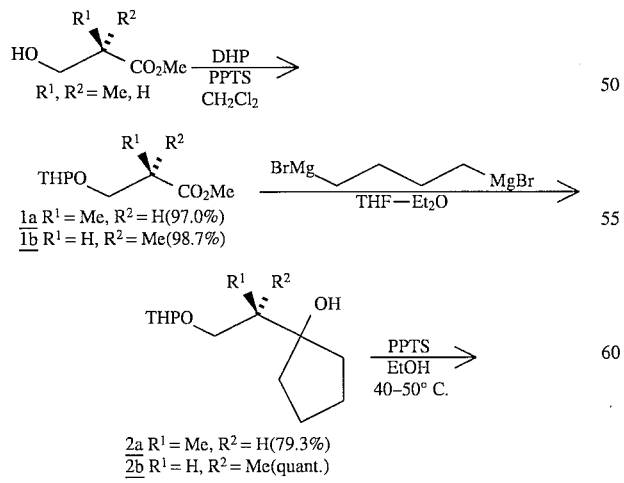

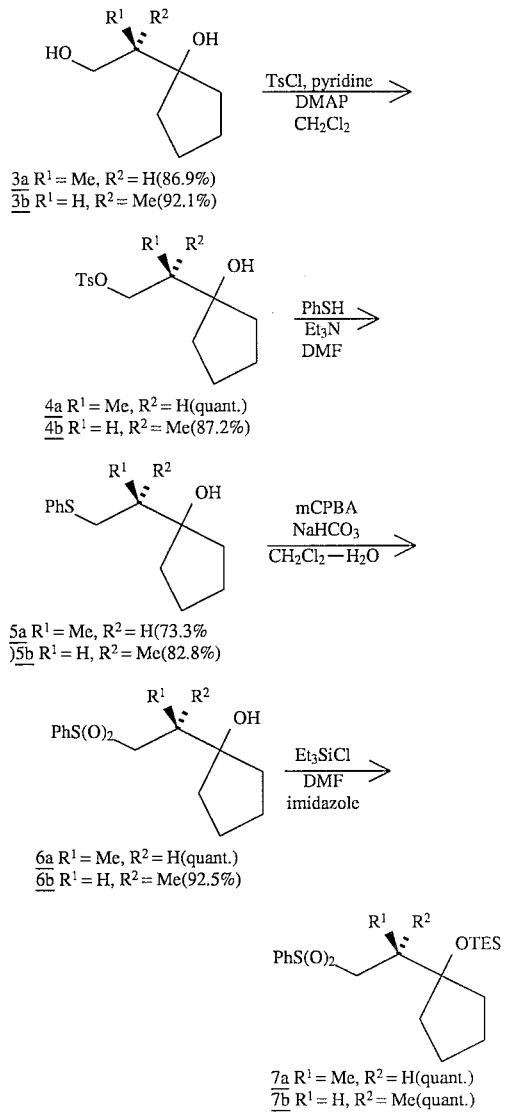

SCHEME II

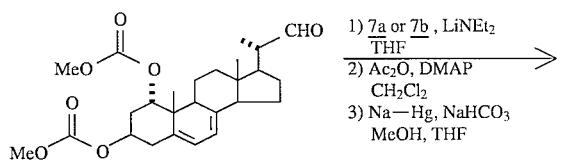

-continued
SCHEME II

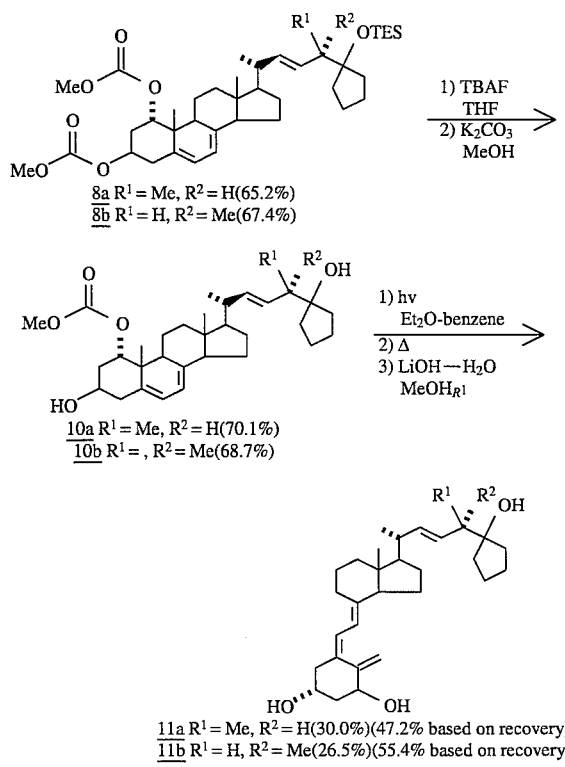

8a R¹ = Me, R² = H (65.2%)
8b R¹ = H, R² = Me (67.4%)

10a R¹ = Me, R² = H (70.1%)
10b R¹ = , R² = Me (68.7%)

11a R¹ = Me, R² = H (30.0%)(47.2% based on recovery)
11b R¹ = H, R² = Me (26.5%)(55.4% based on recovery)

We claim:
1. A compound having the formula

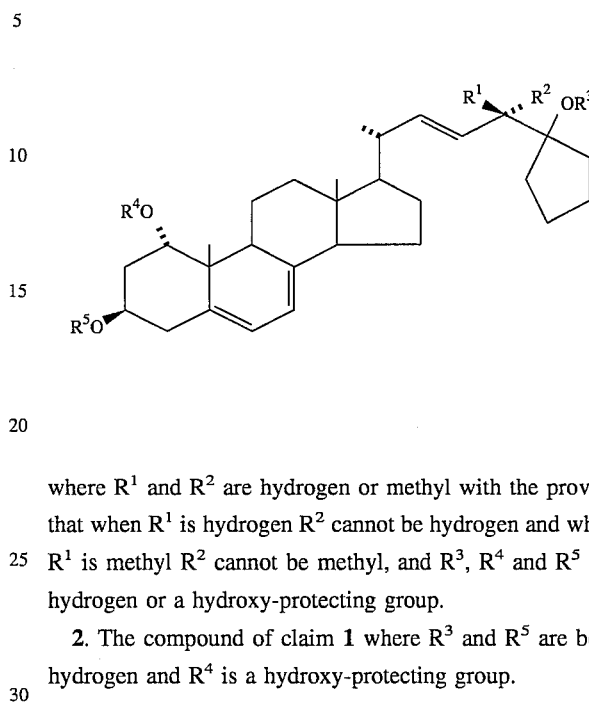

where $R^1$ and $R^2$ are hydrogen or methyl with the proviso that when $R^1$ is hydrogen $R^2$ cannot be hydrogen and when $R^1$ is methyl $R^2$ cannot be methyl, and $R^3$, $R^4$ and $R^5$ are hydrogen or a hydroxy-protecting group.

2. The compound of claim 1 where $R^3$ and $R^5$ are both hydrogen and $R^4$ is a hydroxy-protecting group.

* * * * *